United States Patent [19]

Nielsen

[11] Patent Number: 5,395,622
[45] Date of Patent: Mar. 7, 1995

[54] CALCIUM CHLORIDE CONTAINING PREPARATION FOR THE PREVENTION OR THE TREATMENT OF HYPOCALCEMIA IN RUMINANTS

[75] Inventor: Leif H. Nielson, Nødebo, Denmark

[73] Assignee: Boehringer Ingelheim Agrovet A/S, Hellerup, Denmark

[21] Appl. No.: 25,898

[22] Filed: Feb. 25, 1993

Related U.S. Application Data

[63] Continuation of Ser. No. 679,089, filed as PCT/DK88/00220, Dec. 23, 1988, published as WO 90/07338, Jul. 12, 1990, abandoned.

[51] Int. Cl.$^6$ ............... A01N 59/08; A01N 59/06; A61K 9/48
[52] U.S. Cl. .................... 424/678; 424/696; 424/438; 424/442; 424/451; 424/455; 424/456
[58] Field of Search ............ 424/438, 442, 678, 696, 424/451, 455, 456

[56] References Cited

U.S. PATENT DOCUMENTS

| | | | |
|---|---|---|---|
| 3,642,509 | 2/1972 | Fujimasu | 106/774 |
| 3,996,351 | 12/1976 | Bauer et al. | 424/78.18 |
| 4,185,093 | 1/1980 | Carnes et al. | 424/678 |
| 4,346,077 | 8/1982 | Braund et al. | 424/687 |
| 4,944,957 | 7/1990 | Kingsley et al. | 426/643 |

FOREIGN PATENT DOCUMENTS

| | | |
|---|---|---|
| 365554 | 3/1923 | Germany . |
| 9007338 | 7/1990 | WIPO . |

OTHER PUBLICATIONS

Chemical Abstracts vol. 83 (24): 197819s (1975).
The Merck Index, tenth edition, Rahway, N.J. Merck & Co., Inc., 1983. pp. 229 and 234.
Chemical Abstracts, vol. 34 (1940), Abstract No. 3875, Rev. farm. (Buenos Aires) 81, 15–22, 40–54 (1939).
Chemical Abstracts, vol. 57 (1962), Abstract No. 5560a, Izv. Estestv.-Nauchn Inst. pri Permsk. Univ. 14, No. 4, 67–76 (1960).
Chemical Abstracts, vol. 104 (1986), Abstract No. 219148d, Jpn. Kokai Tokyo Koho JP 61 36, 222 [86 36,222].
"Remington's Pharmaceutical Sciences," 15 Ed., published 1975, Mack Publishing Co. (Easton, Pa.), p. 1258.

*Primary Examiner*—Allen J. Robinson
*Assistant Examiner*—John D. Pak
*Attorney, Agent, or Firm*—Watson, Cole, Grindle & Watson

[57] ABSTRACT

A preparation for the prevention or treatment of hypocalcemia in ruminants is prepared by forming a homogeneous mixture of $CaCl_2 \cdot xH_2O$ and $CaSO_4 \cdot yH_2O$, x being a number greater than 0 and lower than 6 and y being a number equal to or greater than zero and lower than or equal to 2, at a weight ratio of 1:0.05 to 1:2.4, adding water to the mixture to convert the ingredients to $CaCl_2 \cdot 6H_2O$ and $CaSO_4 \cdot 2H_2O$, introducing the mixture into molds, and heating the molds so that the mixture solidifies.

3 Claims, No Drawings

CALCIUM CHLORIDE CONTAINING PREPARATION FOR THE PREVENTION OR THE TREATMENT OF HYPOCALCEMIA IN RUMINANTS

CROSS REFERENCE TO RELATED APPLICATION

This application is a continuation of application Ser. No. 679,089, filed as PCT/DK88/00220, Dec. 23, 1988, published as WO 90/07338, Jul. 12, 1990, now abandoned.

BACKGROUND OF THE INVENTION

The present invention relates to a calcium containing preparation for the prevention or the treatment of hypocalcemia in ruminants.

During the period pending calving when a cow's milk production has normally stopped completely, its calcium mobilisation is also stopped.

Calving sets off a high milk production, and consequently a considerable need for calcium arises. In order to compensate for this sudden need, the body tries to provide calcium from the blood, thus causing the calcium ion content of the blood to decrease drastically. This causes the cow to lose control of its muscles, to lie down and become increasingly apathetic. Unless treated, the cow goes into a coma and dies. This condition is referred to as milk fever. Older cows are particularly prone to milk fever.

It is known to treat milk fever by oral administration to the sick animal of an aqueous calcium chloride solution. The dosage is typically 400 ml solution corresponding to a total amount of about 500 g, and this dosage is typically administered at 12 hour intervals. Aqueous calcium chloride solutions are very unpleasant tasting and therefore the sick animal must be force-treated. This may cause the calcium chloride solution to enter the lungs, which may be fatal to the animal.

In normal practise the calcium chloride solution is replaced with a calcium chloride-containing gel to prevent the therapeutic preparation from entering the lungs. This course of action is only followed for lack of a better one, since the use of a gel poses dosage problems due to the difficulties associated with the discharge of the gel from the container in which it is packed. The use of a gel does not eliminate the taste problem, either.

Attempts have also been made to treat animals suffering from milk fever with capsules containing a powdery calcium compound, such as calcium acetochloride. However, the calcium content of such capsules is relatively low and consequently a considerable number of capsules (e.g. 16) should be administered to the sick animal at two hour intervals, thus rendering the preparation unsuitable for practical use.

SUMMARY OF THE INVENTION

Surprisingly, it has now been found that a solid and easily doseable preparation having a high calcium content may be produced from an aqueous mixture of calcium chloride ($CaCl_2$) and calcium sulphate ($CaSO_4$).

Thus, the preparation according to the invention is characterized in that it is produced by solidification of a mixture of $CaCl_2.xH_2O$ and $CaSO_4.yH_2O$ wherein x is a number equal to or higher than 0 but lower than or equal to 6 and y is a number equal to or higher than 0 but lower than or equal to 2, and water, the weight ratio of $CaCl_2.xH_2O$ and $CaSO_4.yH_2O$ being from 1:0.05 to 1:2.4, and preferably from 1:0.11 to 1:2.4 and the water content being sufficiently high to make the mixture pumpable but constituting no more than the amount required to convert any $CaCl_2.xH_2O$ present into $CaCl_2.6H_2O$ and $CaSO_4.yH_2O$ into $CaSO_4.2H_2O$.

The term "pumpable" denotes that at a temperature of 40° C. the mixture is capable of flowing through a funnel having a neck-diameter of 10 mm.

Immediately upon manufacture a mixture as described above has a typical viscosity like that of double cream. In this state the mixture may readily be enclosed in capsules, e.g. gelatine capsules. After a while, typically 1-2 hours, the mixture solidifies and a solid substance is produced.

The use of the above mixture for the production of calcium-containing gelatine capsules provides the particular advantage that the gelatine is not attacked by the mixture and that a substantially larger amount of Ca (in the form of $Ca^{++}$) may be added to the capsules as compared to the known capsules described above.

The production of the above mixture is preferably carried out by admixing the calcium chloride and the calcium sulphate in their dry state to form a homogeneous mixture. Water is then added and mixing is continued until a pumpable mass is produced. This mass is preferably encapsulated in gelatine capsules in an amount of, e.g. 80–100 g per capsule. The filled gelatine capsules are allowed to stand at a suitable temperature, e.g. at room temperature, for a sufficient period for the mixture to solidify. The solidification is a result of the bonding of the water in the form of crystal water.

Instead of being encapsulated in gelatine capsules, the mixture may be cast to form suitable dosage units. It may also be cast in the form of a coherent mass which may then be disintegrated and ground to form a powder for therapeutic use or for pelleting.

The preparation according to the invention is particularly suitable for the treatment of milk fever, but it is also suitable for the treatment of hypocalcemia in other ruminants, e.g. sheep.

The invention will now be described in further detail with reference to the following example.

EXAMPLE

Calcium containing gelatine capsules were produced as follows from solid $CaCl_2.2H_2O$ and $CaSO_4.\frac{1}{2}H_2O$:

The solids were mixed in the amounts given in Table 1 below in a Björn mixer. Water was added to the mixture and mixing was continued for another 10-20 minutes until the mixture was homogeneous and easy-flowing. The mass thus obtained was then enclosed in gelatine capsules and the filled capsules were allowed to stand for 24 hours at room temperature in an airtight compartment.

The capsules were then packed in an airtight package.

TABLE 1

| Test | $CaCl_2.2H_2O$ gm | $CaSO_4.\frac{1}{2}H_2O$ gm | $H_2O$ gm | $CaCl_2:CaSO_4$ Mixture ratio |
|---|---|---|---|---|
| a: | 1000 | 0 | 520 | 1:0 |
| b: | 900 | 100 | 180 | 1:0.11 |
| c: | 800 | 200 | 170 | 1:0.25 |
| d: | 700 | 300 | 150 | 1:0.43 |
| e: | 600 | 400 | 150 | 1:0.67 |
| f: | 500 | 500 | 150 | 1:1.00 |
| g: | 400 | 600 | 170 | 1:1.50 |
| h: | 300 | 700 | 220 | 1:2.33 |
| i: | 200 | 800 | 350 | 1:4.00 |
| j: | 100 | 900 | 630 | 1:9.00 |

TABLE 1-continued

| Test | $CaCl_2.2H_2O$ gm | $CaSO_4.\frac{1}{2}H_2O$ gm | $H_2O$ gm | $CaCl_2:CaSO_4$ Mixture ratio |
| --- | --- | --- | --- | --- |
| k: | 0 | 1000 | 1200 | $1:\infty$ |

Testing of the capsules produced yielded the results given in Table 2.

TABLE 2

| Test | Solidification time, h | "Pumpability" | Compatibility with gelatine capsule | $Ca^{++}$ in filled capsule (gm) |
| --- | --- | --- | --- | --- |
| a: | partial solidification, 1/2 | poor | incompatible | 14.6 |
| b: | 1/2 | moderate | moderate | 19.6 |
| c: | 1-2 | good | " | 20.1 |
| d: | 3-6 | " | good | 20.6 |
| e: | 6-12 | " | " | 21.1 |
| f: | 12-18 | " | " | 21.4 |
| g: | 12-18 | " | " | 21.2 |
| h: | 18-24 | " | moderate | 20.6 |
| i: | >24 | " | incompatible | 19.0 |
| j: | >24 | " | " | 16.1 |
| k: | >24 | " | " | 12.3 |

As will appear from Table 2, only tests b-h employing the preparations according to the invention yields satisfactory results as regards both solidification time, compatibility with the gelatine capsule and the Ca content of the capsules.

The above results show the surprising synergistic effect of the simultaneous use of calcium chloride and calcium sulphate in admixture with water both as regards the compatibility of the mixture with gelatine capsules, pumpability and solidification time.

The surprising effect may be illustrated by comparative tests using (1) a mixture of 50 parts by weight of $CaCl_2.2H_2O$ 50 parts by weight of $CaSO_4.\frac{1}{2}H_2O$ and 15 parts by weight of water, (2) a mixture of 50 parts by weight of $CaCl_2.2H_2O$ and 15 parts by weight of water and (3) a mixture of 50 parts by weight of $CaSO_4.\frac{1}{2}H_2O$ and 15 parts by weight of water.

Whereas mixture (1) provides the desired compatibility with gelatine capsules and a satisfactory pumpability and solidification time, mixture (2) forms a paste of crystals which is unpumpable and solidifies too quickly and which is also incompatible with gelatine capsules, and mixture (3) forms a mass which is neither pumpable nor castable.

I claim:

1. A method of providing dosage units containing calcium for administering to ruminants to treat hypocalcemia, said method comprising the steps of
   (a) mixing $CaCl_2.xH_2O$ and $CaSO_4.yH_2O$, x being a number greater than 0 and lower than 6 and y being a number equal to or greater than 0 and lower than or equal to 2, the weight ratio of $CaCl_2.xH_2O$ to $CaSO_4.yH_2O$ being from 1:0.05 to 1:2.4, to form a homogeneous mixture,
   (b) adding water to said homogeneous mixture to provide a mass which will flow through a funnel having a neck diameter of 10 mm at 40° C., the amount of water not exceeding the amount needed to convert $CaCl_2.xH_2O$ to $CaCl_2.6H_2O$ and $CaSO_4.yH_2O$ to $CaSO_4.2H_2O$,
   (c) introducing said mass into a plurality of casting moulds, and
   (d) subjecting said mass contained in said moulds to a temperature such that said mass solidifies therein into a solid mass containing a mixture of $CaCl_2$ and $CaSO_4$ hydrates.

2. A method according to claim 1, wherein in step (c) individual portions of said mass are respectively encapsulated within individual gelatine capsules.

3. A method according to claim 1, wherein in step (a) said weight ratio is 1:0.11 to 1:2.4.

* * * * *